(12) United States Patent
Divisi

(10) Patent No.: US 11,020,504 B2
(45) Date of Patent: Jun. 1, 2021

(54) ENVIRONMENTAL SANITIZING DEVICE AND METHOD THEREFOR

(71) Applicant: DROPSA S.p.A., Milan (IT)

(72) Inventor: Walter Divisi, Monaco (MC)

(73) Assignee: DROPSA S.P.A., Milan (IT)

( * ) Notice: Subject to any disclaimer, the term of this patent is extended or adjusted under 35 U.S.C. 154(b) by 198 days.

(21) Appl. No.: 16/002,002

(22) Filed: Jun. 7, 2018

(65) Prior Publication Data

US 2018/0353632 A1    Dec. 13, 2018

(30) Foreign Application Priority Data

Jun. 9, 2017    (IT) .................... 102017000064070

(51) Int. Cl.
*A61L 2/22*    (2006.01)
*A61L 2/24*    (2006.01)
(Continued)

(52) U.S. Cl.
CPC ............. *A61L 2/22* (2013.01); *A61L 2/186* (2013.01); *A61L 2/24* (2013.01); *A61L 9/14* (2013.01);
(Continued)

(58) Field of Classification Search
CPC ... A61L 2/22; A61L 2/186; A61L 2/24; A61L 2/26; A61L 9/14; A61L 2202/25;
(Continued)

(56) References Cited

U.S. PATENT DOCUMENTS 4,823,268 A * 4/1989 Giles .................... A01M 7/0089
239/77
6,897,466 B2 * 5/2005 Teramae .................... B41J 2/01
250/576

(Continued)

FOREIGN PATENT DOCUMENTS

EP    1801538 A2    6/2007
EP    2618853    7/2013
(Continued)

OTHER PUBLICATIONS

Search Report and Written Opinion dated Mar. 20, 2018 for Italian patent application No. 2017000064070.

*Primary Examiner* — Regina M Yoo
(74) *Attorney, Agent, or Firm* — Vorys, Sater, Seymour and Pease LLP

(57) ABSTRACT

Environmental sanitizing device including a frame housing a disinfectant liquid reservoir and supporting a nozzle, the nozzle associated with a generation system of an air flow within which a plurality of disinfectant liquid particles are suspended to sanitize a closed environment in which the device can be positioned; the nozzle is movable with respect to the frame, and associated with positioning system controlled by a control unit for orientation of the nozzle with respect to at least two mutually perpendicular axes, preferably around a first vertical axis and around a second horizontal axis to automatically orient the nozzle in desired direction with respect to the frame during a sanitization step, the nozzle coupled with at least one distance detector able to determine distance between the nozzle and an obstacle facing the nozzle.

18 Claims, 4 Drawing Sheets

(51) Int. Cl.
    *B05B 12/12*     (2006.01)
    *A61L 9/14*     (2006.01)
    *B05B 7/00*     (2006.01)
    *A61L 2/18*     (2006.01)
    *B05B 15/656*     (2018.01)
    *B05B 15/652*     (2018.01)
    *B05B 7/24*     (2006.01)
    *B05B 15/628*     (2018.01)

(52) U.S. Cl.
    CPC .......... *B05B 7/0012* (2013.01); *B05B 7/0093* (2013.01); *B05B 12/12* (2013.01); *B05B 12/124* (2013.01); *B05B 15/652* (2018.02); *B05B 15/656* (2018.02); *A61L 2202/14* (2013.01); *A61L 2202/15* (2013.01); *A61L 2202/25* (2013.01); *B05B 7/2491* (2013.01); *B05B 15/628* (2018.02)

(58) Field of Classification Search
    CPC ............. A61L 2202/14; A61L 2202/15; A61L 2209/134; B05B 12/124; B05B 15/656; B05B 12/12; B05B 15/652; B05B 7/0093; B05B 7/0012; B05B 7/2491; B05B 15/628
    See application file for complete search history.

(56) References Cited

U.S. PATENT DOCUMENTS

| | | | | |
|---|---|---|---|---|
| 8,602,396 | B1* | 12/2013 | V | A61L 9/122 239/DIG. 11 |
| 8,875,655 | B2* | 11/2014 | Pettersson | B05B 12/122 118/713 |
| 9,386,889 | B2* | 7/2016 | Fischer | A47K 3/28 |
| 9,469,278 | B2* | 10/2016 | Wimmer | B60S 3/06 |
| 2008/0004846 | A1* | 1/2008 | Onozuka | G06F 30/20 703/9 |
| 2011/0073675 | A1 | 3/2011 | Wolosuk | |
| 2013/0199540 | A1* | 8/2013 | Buske | A61B 18/042 128/845 |
| 2013/0199582 | A1* | 8/2013 | Petit | B08B 3/024 134/123 |
| 2013/0239992 | A1* | 9/2013 | Detrick | B60S 3/06 134/18 |
| 2014/0076985 | A1* | 3/2014 | Pettersson | B05B 7/0846 239/11 |
| 2015/0052678 | A1* | 2/2015 | Bayley | E03C 1/181 4/638 |
| 2015/0274294 | A1* | 10/2015 | Dahlstrom | B05B 13/0278 239/722 |
| 2016/0008834 | A1* | 1/2016 | Brudevold | F04B 19/22 427/8 |
| 2016/0095947 | A1 | 4/2016 | Malaguti Simoni et al. | |
| 2016/0368005 | A1* | 12/2016 | Pajel | B05C 9/12 |
| 2017/0203318 | A1* | 7/2017 | Vahanen | B05B 15/652 |
| 2018/0169682 | A1* | 6/2018 | Miller | B05B 12/122 |

FOREIGN PATENT DOCUMENTS

| | | |
|---|---|---|
| EP | 2991690 | 3/2016 |
| WO | 03082355 A1 | 10/2003 |
| WO | 2009046561 A2 | 4/2009 |
| WO | 2013169328 A1 | 11/2013 |
| WO | 2015116876 A1 | 8/2015 |

* cited by examiner

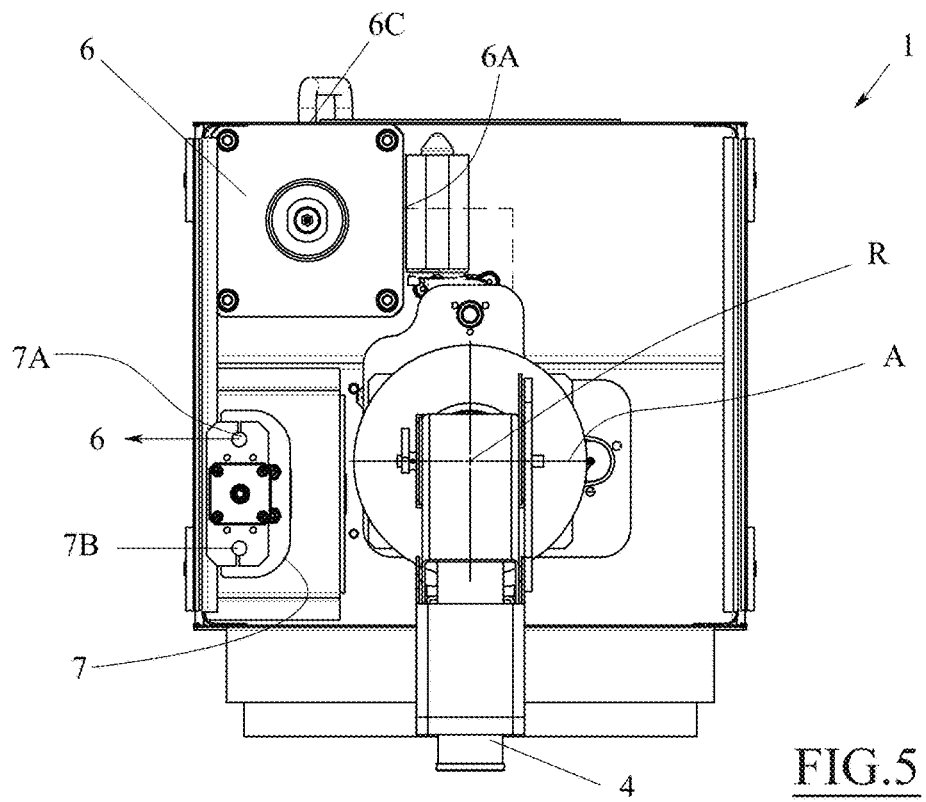
FIG.5
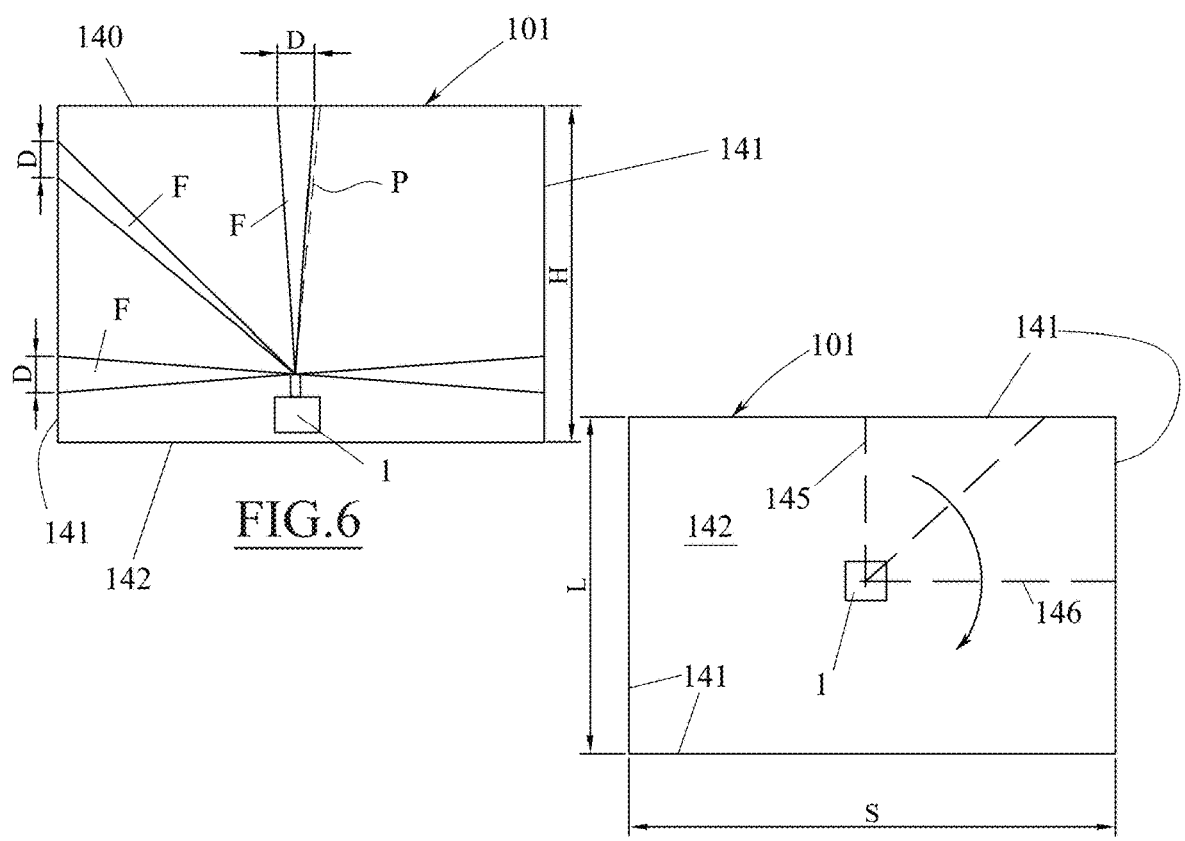
FIG.6
FIG.7

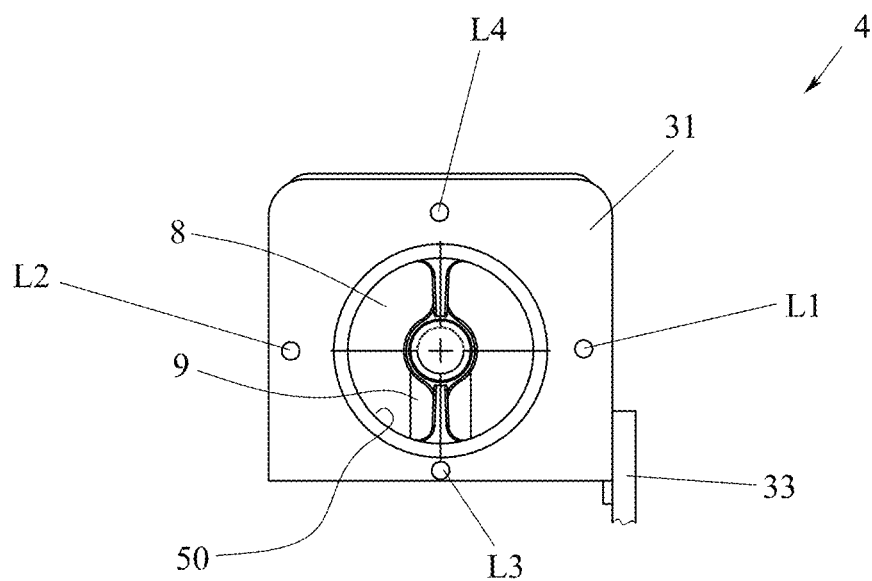
FIG.8
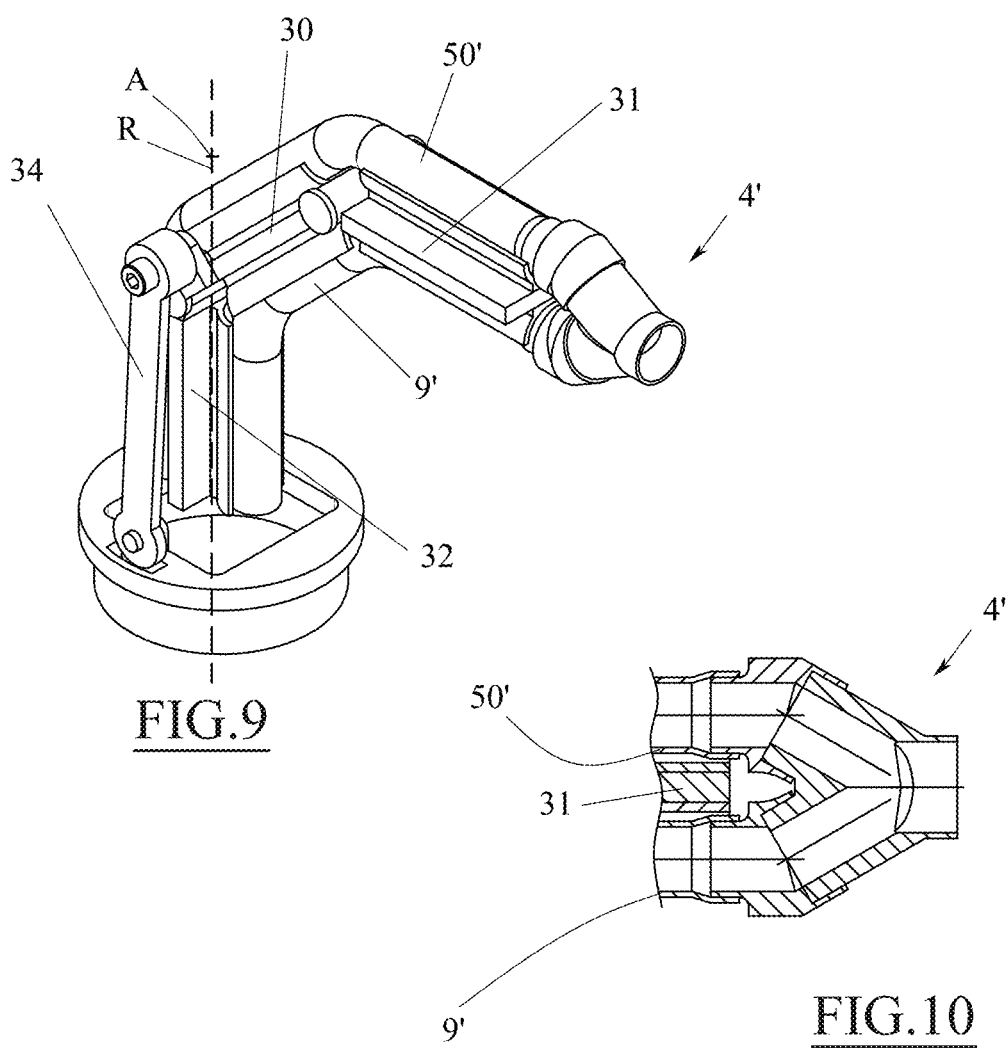
FIG.9
FIG.10

ENVIRONMENTAL SANITIZING DEVICE AND METHOD THEREFOR

CROSS REFERENCE TO RELATED APPLICATION

This claims the benefit of Italian patent application no. 102017000064070, filed Jun. 9, 2017, incorporated herein by reference in its entirety.

FIELD OF THE INVENTION

The present invention relates to an environmental sanitizing device and method therefor.

In particular, the invention refers to a device and a method of sanitizing a closed environment by means of an air flow within which a plurality of fine particles of a disinfectant liquid are suspended.

BACKGROUND ART

There are various commonly known devices for environmental sanitation, such as those described in patent documents EP2991690-A1 and EP2618853-A1.

Such devices do not provide effective sanitization of the environments in which they can be positioned and are complicated to use.

SUMMARY OF THE INVENTION

The object of the present invention is to provide a sanitizing device and method which are improved compared with those described in the prior art.

This and other objects are achieved by means of a device and method according to the technical teachings of the claims annexed hereto.

BRIEF DESCRIPTION OF THE FIGURES

Further characteristics and advantages of the invention will become apparent in the description of a preferred but not exclusive embodiment of the invention, illustrated—by way of a non-limiting example—in the drawings annexed hereto, in which:

FIG. 5 is an overhead view of the device in FIG. 1;

FIG. 6 and FIG. 7 are schematic views of an environment inside which the device in FIG. 2 is positioned, in which some of the sanitizer operating steps are illustrated FIG. 8 is a simplified enlargement of a detail of the device in FIG. 2;

FIG. 9 is a simplified perspective view of a different embodiment of a part of the device in FIG. 1; and FIG. 10 is a simplified section of an end of a nozzle on part of the device in FIG. 9.

DETAILED DESCRIPTION OF THE INVENTION

With reference to the figures stated, reference number 1 is used to denote, as a whole, a sanitizing device.

Figure 1:
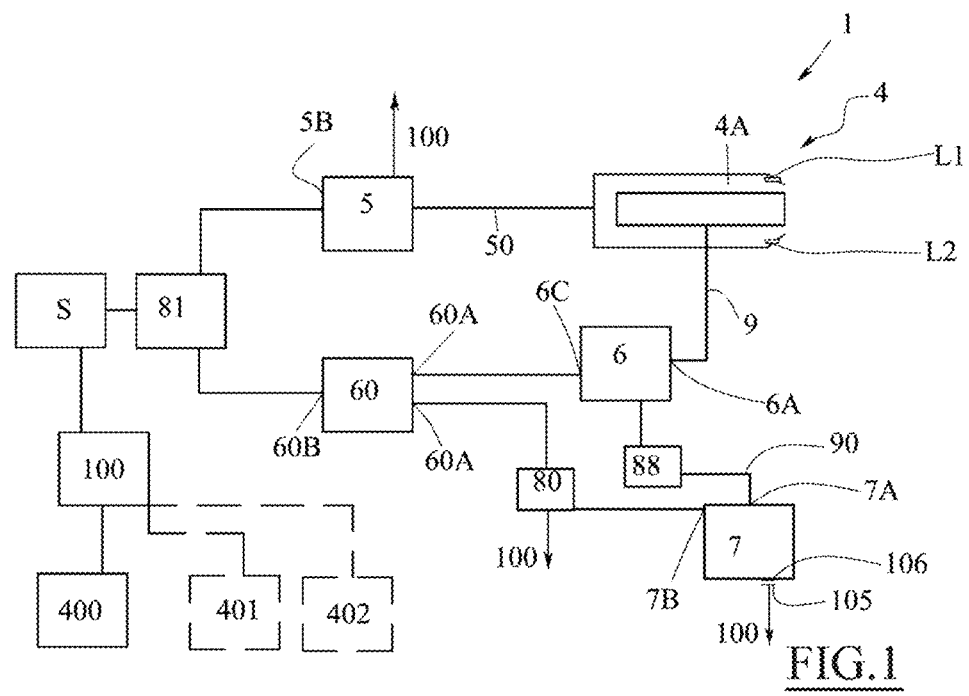
FIG. 1 is a schematic view of a device according to the present invention.

The environmental sanitizing device 1 according to the present invention is shown schematically, in terms of the main components thereof, in FIG. 1. FIGS. 2 to 5 and FIG. 8 show a 'physical' embodiment of the sanitizing device in a configuration without a casing, to highlight some of the components schematized in FIG. 1.

Figure 2:
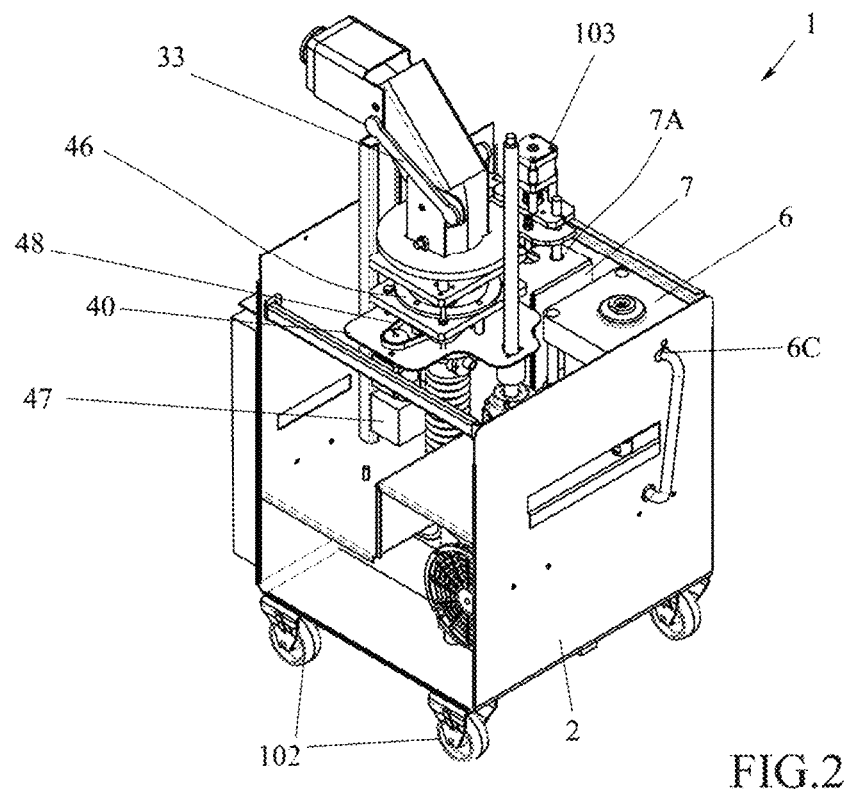
FIG. 2 is a simplified perspective view of a device incorporating the components schematized in FIG. 1, in which some parts of the casing and some components have been removed for the sake of clarity of representation.

Obviously the configuration shown in FIG. 2 and the following figures is provided purely by way of example. For example, many auxiliary parts (not shown here) may be added to the configuration shown in order to lend the sanitizing device pleasant, modern aesthetics.

As can be seen however, especially in FIG. 2, the device is configured to be transportable from room to room, preferably by hand and possibly with the aid of wheels 102, associated with a frame 2 supporting all the components.

In order to facilitate transportation within the environment 101 one wishes to sanitize (usually a room, an operating room, or any other environment, although preferably indoors), one or more gripping handles (not shown) may be featured in order to allow easy lifting and/or transportation of the device 1. Advantageously, the gripping handle(s) (which have, for example, a single upright) may feature a locking system for one or more of the wheels 102 on the device 1, to prevent vibrations coming from internal propellers (which will be described later on) moving the device during a sanitization step.

Specifically, the device 1 comprises a frame 2 (mounted, as stated earlier, on wheels 102) which houses and supports at least one reservoir 7 of a disinfectant liquid 3, which is preferably removable and disposable.

The reservoir or cartridge 7 may feature sufficient capacity to perform one or more sanitization cycles. For example, the said reservoir may have a capacity of 1 litre of a liquid-phase disinfectant product. By way of example, the liquid-phase disinfectant may be a solution of hydrogen peroxide and silver cations. Nevertheless, other types of known disinfectant products may be used.

Preferably, the device houses a single cartridge 7 only. The latter may feature an inlet 7B and an outlet 7A, advantageously located in a raised area, when the cartridge 7 is housed in the device 1.

The inlet and outlet may be protected by a removable membrane (or other safety system or device), which is used as an anti-tamper seal. The seal may also state the cartridge manufacture data, expiry date, etc., but will also serve as a safety measure to prevent spillage of the liquid contained therein.

The securing and perforation of the reservoir/cartridge 7 may take place automatically, for example by means of a motorized system 103, or other suitable system for sealing a system securing a reservoir or a door (not shown) of a compartment in the device 1 inside which the reservoir may be housed. The compartment housing the reservoir is preferably featured on the side or rear of the device, in order to allow the other components of the sanitizing device to be housed inside the frame.

The automatic system for perforating the reservoir 7 may be provided to reduce the risk of contamination of an operator (in the event thereof) with the product contained in the reservoir.

An RFID tag 106 may be featured on each cartridge 7, in order for a control unit 100 (featured on the device 1 to manage all the functions thereof) to verify the authenticity of the cartridge inserted, the expiry date thereof, the possible concentration or the type of disinfectant liquid, or other useful information envisaged in the design step. For this purpose, the control unit 100 may be interfaced with an RFID reader 105, which is located in proximity to the reservoir. The control unit 100 may independently verify the originality of the cartridge, or it may be connected via a communication interface 400 to an external server, which manages the verification operations on the basis of certain data stored in the RFID chip.

The frame 2 of the device 1 supports an orientable nozzle 4. The nozzle 4 is supplied by a system which generates an air flow within which a plurality of disinfectant liquid particles is suspended, so as to sanitize a closed environment 101 in which the device 1 may be positioned.

In order to generate a flow of air and disinfectant, the orientable nozzle 4 may be in fluid communication with a delivery line 5A on a blower 5 and with a nebulizer 6 for the said disinfectant liquid taken from the aforesaid reservoir 7.

Figure 4:
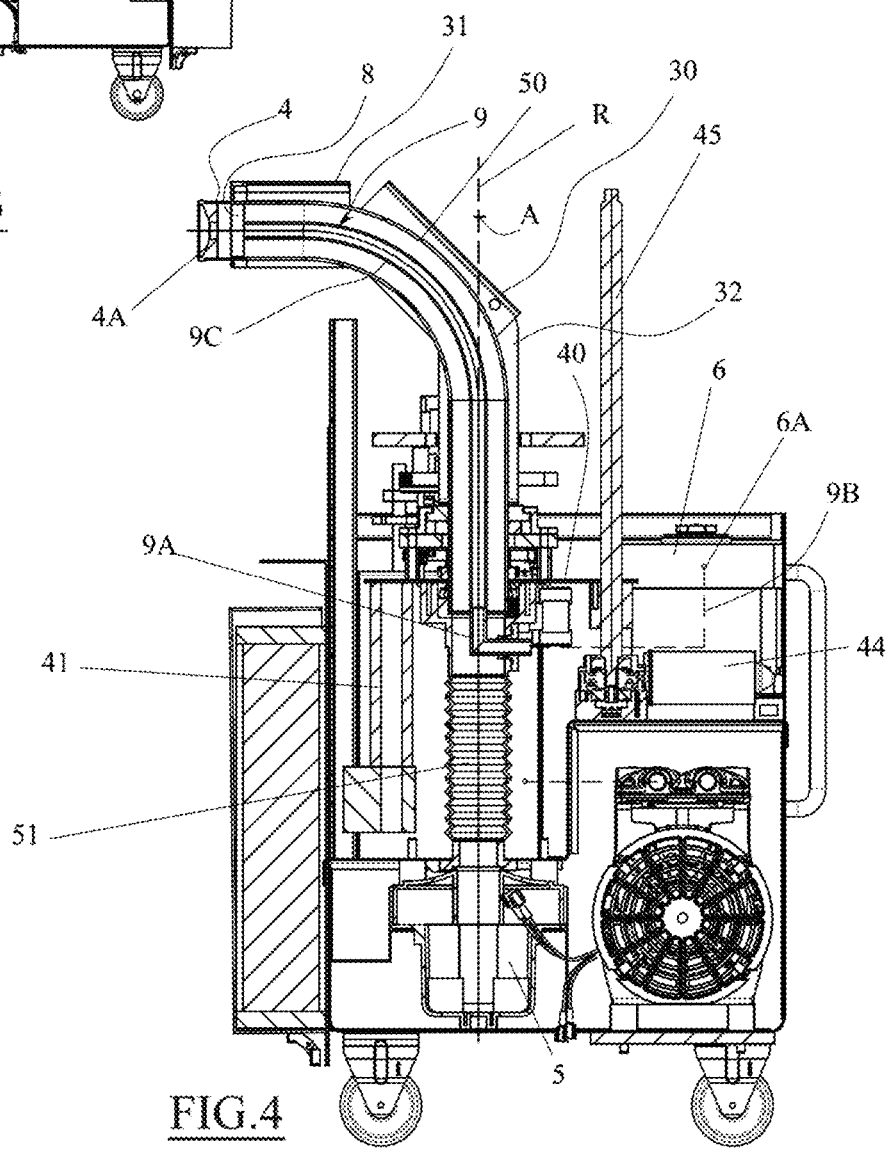
FIG. 4 is a simplified side section of the device in FIG. 1 with some parts of the casing removed.

As may be seen in FIG. 4, the nozzle 4 may feature (at least in proximity to an outlet section 4A thereof) a channel supplied by the blower delivery line in which a mist line 9 flows, the said mist line being connected to the outlet 6A of the nebulizer 6.

The channel supplied by the blower 5, in proximity to the nozzle outlet section, is preferably annular (see FIG. 8). In this way, the flow of particles (or mist) that is delivered by the mist line 9 remains well confined by the annular air flow coming out of the nozzle.

Furthermore, a convergent-shaped nozzle may be featured, which accelerates the air flow velocity, in particular in the external, annular part of the flow, thereby creating an annular secondary air flow which moves at a different speed from the main flow. In this way, the main air flow is circumscribed and containment of the particles is possible.

Specifically, the terminal end of the mist line 9 may be supported by fins 108 forming part of the nozzle, so as to maintain the said end in a central position with respect to the nozzle 4.

The mist line 9 may feature a first section 9C produced by means of a hose connected to a fitting 9A (for example a 90° fitting) connected to a further piece of hose 9B (shown schematically) connected to the outlet 6A of the nebulizer 6.

The nozzle 4 may, instead, be connected to the outlet 5A of the blower 5 by means of a hose 50 with a large diameter (inside which at least the first portion 9C of the mist line 9 may pass), and a tubular bellows portion 51 (the utility of which will be explained later on).

The blower 5, which may be of the turbine type with an axial or radial flow, may comprise a motor which may be controlled in such a way as to vary the number of revolutions of an impeller, thereby varying the power of the said blower.

For example, the motor associated with the blower will have a power of over 1000 W. It may be connected to a revolution multiplier (for example of the planetary kind) in order to achieve an impeller rotation speed ranging from 7000 to 22000 rpm. The number of revolutions may be controlled by the control unit 100 interfaced with the blower 5.

The blower 5 connected to the nozzle 4 may be optimised (in terms of air flow) to efficiently treat surfaces which are up to 10 metres away from the nozzle, based on an optimization involving the maximum number of revolutions of the motor.

The orientable nozzle 4 may be associated with a positioning system 21, 22 for the orienting thereof with respect to at least one axis R around which it may rotate, but preferably around at least two mutually angled axes R. For example, the first axis is a vertical axis R and the second axis is a horizontal axis A with respect to the device 1 support plane (the floor). In this case, the axes are mutually orthogonal.

In addition, the nozzle 4 may be shifted (including therein by means of automatic devices 45, 44) along the vertical axis R, so as to be retracted (at least partially) when the device 1 must be transported (so as to minimize the overall dimensions thereof). Hence the purpose of the bellows portion 51 of the hose described earlier, which provides such positioning.

In order for the nozzle 4 to be movable along the axis R, the said nozzle may be supported by a plate-shaped element 40 equipped with guides 41 associated with the frame 2. The plate-like element 40 may be moved along the first vertical axis R by a first gear motor 44 coupled to a worm screw 45 suitably engaged with the plate-like element. Obviously, the configuration described is just one of the many possible configurations which may be used to achieve this type of vertical positioning.

The rotation of the nozzle 4 around axis R (yaw) is possible, meanwhile, since the nozzle 4 may be mounted on a slewing bearing 46 (for example, supported by the plate-like element), with a vertical axis R, rotated by a gear motor 48 with belt transmission 49. Advantageously, this configuration allows 360° rotation of the nozzle, compatibly with the abundance and flexibility of the portion 9B of the hosing 9.

Figure 3:
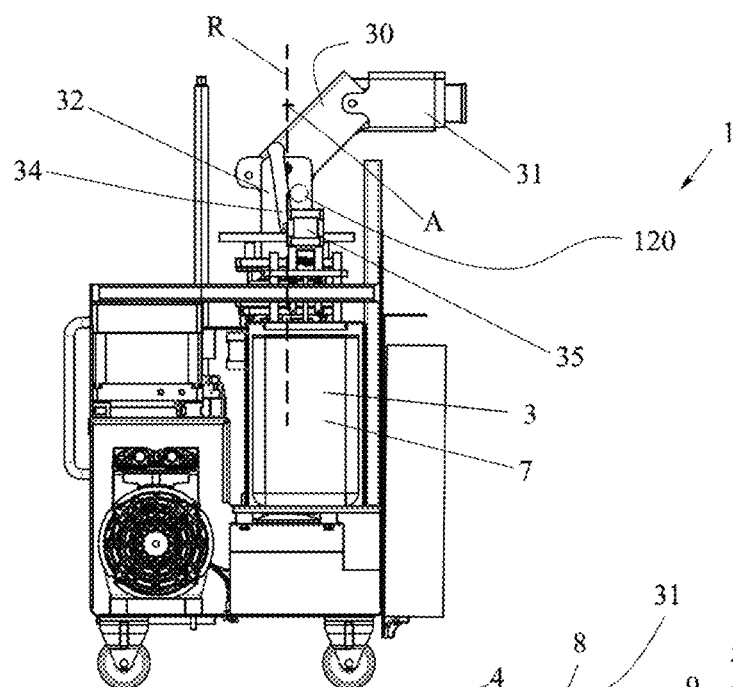
FIG. 3 is a simplified side view of the device in FIG. 2 with some parts removed.

The rotation of the nozzle around axis A (pitch) is possible, due to the fact that the nozzle 4 may be supported by a first 30 and a second body 31 (for example, box-shaped structures). The first box-shaped body 30 may be hinged to a support 32, while the second box-shaped body 31 may be hinged to the first box-shaped body 30. Furthermore, as can be seen in FIGS. 2 and 3, the second box-shaped body 31 may be connected to the support 29 by a first connecting rod 33, while the first box-shaped body may be connected, by means of a second connecting rod 34, to a gear motor 35 for controlling rotation of the nozzle around the horizontal axis A. Rotation around axis A may be limited to 90°.

A rotation of the gear motor 35 causes movement of the connecting rod 34 which transmits movement to the first box-shaped body 30. Since the first box-shaped body 30 is hinged to the second box-shaped body 31, the latter moves, in turn, with a movement guided by the first connecting rod 33. A very fluid positioning of the nozzle 4 around the horizontal axis A (rotation or rotational shift) is thus possible.

The particular kinematic mechanism of the system described above makes it possible to prevent or minimize potential crushing of the hoses 9 and 50 housed inside the bodies and the support 32 which, according to the present description, may have a hollow configuration with a square, rectangular, hexagonal, circular, or other suitable section.

Only some or all of the gear motors or motors that drive the movements described above may be interfaced with the control unit 100, which controls the positioning thereof in the way explained later on.

Advantageously, the nozzle 4 is associated with at least one distance detector L1, L2, L3, L4 envisaged to determine the distance between the nozzle (or rather the outlet section 4A thereof) and an obstacle facing the latter. The distance detectors may be interfaced with the control unit 100.

For example, a first L1 and a second distance detector L2 may be positioned at the sides of the nozzle (horizontally aligned) so that the first detector is operative when the nozzle rotates around the R axis towards the first detector L1

(anticlockwise then), while the second detector L2 is operative when the nozzle rotates in the opposite direction.

Optionally, a third L3 and a fourth distance detector L4 may also be featured, positioned below and above the nozzle (vertically aligned) so that the third detector is operative when the nozzle 4 rotates around axis A towards the latter (lowering), while the fourth detector L4 is operative when the nozzle rotates in the opposite direction.

Advantageously, one or more detectors (for example of the laser kind) are installed directly onto the nozzle, or onto the box-shaped element which supports it.

The installation of each detector may be such that an axis of the pointing line P of the distance detector (see FIG. 6) is outside the flow F emitted by the nozzle. In this way, the flow emitted by the nozzle does not interfere with the detector reading, and the detector may 'see' any obstacles placed 'further ahead' (in the nozzle rotation direction at a specific time) with respect to the point where the flow is concentrated.

In order to generate a homogeneous dispersion of the particles of disinfectant liquid inside the air flow generated by the blower 5, a nebulizer 6 may be used, inside which the mist subsequently conveyed to the nozzle 4 is generated.

To allow the operation of a stand-alone nebulizer 6 which is separate from the nozzle 4, a compressor 60 may be featured whose delivery line 60A is connected to a pressurized air inlet 6A of the nebulizer 6.

In essence, a configuration such as the one described allows a mist to be generated (with particles of a controlled size) inside the nebulizer 6, and—once the mist has been generated—pushed out (or sucked in) towards the nozzle 4 (or in any case, the hosing featured downstream of the blower 5).

The coupling, within the same system, of a nebulizer 6 powered by a compressor (therefore, with high pressure and low flow rates) for generating the mist, and a blower (therefore, with low pressure and high flow rates) to push the mist into the environment to be sanitized, allows the generation of a highly efficient sanitizing flow.

To deliver the liquid taken from the reservoir 7 to the nebulizer 6, a delivery line 60A on the compressor 60 may be connected to an inlet 7B of the reservoir 7 (so as to pressurize the said liquid).

Also between the delivery line 60A on the compressor 60 and the inlet 7B of the reservoir 7, a solenoid valve 80 may be positioned (interfaced with the control unit 100), which controls the inflow of compressed air to the reservoir 7 when necessary.

In order to appropriately control and regulate the amount of liquid supplied to the nebulizer 6 and, optionally, calculate the amount of liquid remaining in reservoir 7, a flow meter 88 may be featured on a pipe 90 connecting the outlet of the reservoir 7A and the inlet of the nebulizer 6. Obviously, the flow meter is interfaced with the control unit 100, also to allow the latter to appropriately establish and signal when the reservoir is empty or running low, and/or to manage any automatic reordering of a new cartridge, for example through the communication interface 400 (in communication with an external server 402) which will be discussed later on.

The nebulizer 6 may feature an integrated reservoir for the recovery of the condensed part of the particles nebulized thereinside. The integrated reservoir may also directly receive the liquid from the cartridge 7 and the mist generation liquid may be drawn directly from the said integrated reservoir.

The compressor 60 may comprise a BLDC motor whose speed is regulated by the control unit 100. For example, the amount of sanitization liquid to be sprayed (and therefore the amount sent from the reservoir to the nebulizer) during the length of time may be 100 cc over 10 minutes of operation with the blower 5 operating at maximum capacity.

Control of the amount of liquid sent to the nebulizer 6 is managed by the solenoid valve 80, also on the basis of the reading by the flow meter 88.

To complete the mechanical description of the device 2, it should be noted that an inlet 60B of the compressor and an inlet 5B of the impeller may be connected to a common filtering element 81.

Furthermore, for example before the filter 81, a sensor S may be featured, envisaged to detect the quantity of disinfectant particles present in the air sucked in by at least the blower 5 (and therefore present in the environment to be sanitized) so as to establish the duration of the sanitization cycle and the termination thereof (which may be determined, for example, by the absence of disinfectant particles in the intake air).

In addition, the device 1 may provide, in a clearly visible position, a signal light 120 (FIG. 3) showing the progress or completion of a sanitization procedure. The light, controlled by the control unit 100, may take on three different statuses (for example red, yellow, or green). A first status (for example, red) may show that a sanitization process is in progress, during which disinfectant liquid is emitted via the nozzle. A second status (for example, the yellow light) may show a break, during which disinfectant liquid is no longer being emitted and the particles are expected to settle and act (and therefore it is not possible to enter the environment 101). A third status (for example, the green light) may show a completed sanitization process, at which point it is possible to enter the sanitized environment without risk.

As mentioned in various parts of the description, it must be emphasized that the device is equipped with the control unit 100, which is interfaced with all the electrical devices (motors, actuators, impeller, compressor) and the electronic devices (sensors, detectors, etc.) which determine operation of the various parts of the device 1.

The control unit 100 may also be connected to a user interface, which can display device information and operating procedures on a screen (for example, a resistive touch screen). Using the touch screen, the sanitization cycles may be activated and the parameters necessary for correct operation of the device may be set, although, preferably, the device has an essentially automatic operation. The touchscreen is appropriately protected to prevent problems relating to contamination deriving from the liquid used for sanitization.

The device may also be controlled remotely (for example via a mobile phone with a Bluetooth connection or other wireless connection) in order to manage the activation and the various steps of the sanitization cycle, including therein from outside the room where the sanitization is carried out.

Furthermore, the control unit 100 may be interfaced with a GPS sensor, and therefore be able to create a certified log of the sanitization cycles carried out, the duration thereof, etc. (for use in healthcare facilities, if necessary), which may also include the location of the treated environment.

More specifically, the control unit 100 may record sanitization data in an integrated internal memory (not shown). Furthermore, it may acquire a position (geolocation) of the environment or room where the sanitizer is located. The acquisition of the position may take place directly via a GPS device 401 optionally integrated into the device 1, or the position may be sent to a communication board 400 (preferably via wireless, WiFi, or Bluetooth connection), associated with the control unit 100, which interfaces with an external geolocation system or an external device. Thus, through the communication board 400, the position of the device 1 may be acquired, for example, by a smart device such as a smartphone/tablet. It is also possible to enter the position of the room or environment where the device is located 1 manually, using the smart device.

The information acquired may be included in a certification or sanitization report for the room, which may also include one or more of the following additional types of information: position, description of the sanitization place, date, and time, result of the sanitization, duration of the sanitization, amount of liquid used for the sanitization, sanitization liquid production date, production batch, and production place (acquired via the RFID of the liquid used for sanitization), etc.

The control unit 100, appropriately interfaced through authentication with an external server 402 (directly or, again, through the communication card 400), may store the certification data described above in a centralized database (e.g. iCloud), thus allowing different (authenticated) devices to check whether the room has effectively been sanitized and the sanitization specifications.

The control unit 100, once appropriately interfaced with a server 402, may also manage automatic reordering of the sanitization liquid when the said liquid is running low.

The control unit 100 may be configured to carry out the following method, according to which the said unit can operate a device according to the present invention.

The method may therefore be implemented using a device featuring a nozzle 4 which may be rotated along at least one, but preferably two axes, wherein the air flow generated by a blower and a flow of nebulized disinfectant liquid converge.

Preferably, a mist of fine particle disinfectant liquid, generated by a nebulizer, is introduced into the stream of air devoid of sanitizing particles. Preferably, the particle size is below 1 micron and even more preferably below 0.5 micron.

The method may include the following steps:

a. pointing the nozzle in a predetermined direction, and detecting the distance between the sanitizing nozzle (or an outlet section thereof) and an obstacle facing the nozzle, and subsequently b. regulating the power of the blower injecting air into the nozzle, according to the distance detected, in order to obtain an area of flow impact on the obstacle which is essentially uniform.

An area D of flow impact on the object which is essentially uniform or the same from different distances, is achievable by ensuring the speed of the flow upon impact on a distant object is the same as the speed of the flow upon impact on a nearby object. By regulating the power of the blower according to the distance between the object and the nozzle, it is possible to achieve the said result.

Furthermore, when—following nozzle positioning—the distance detected between the nozzle and the obstacle decreases, the blower power may be decreased; conversely, when—following further nozzle positioning—the distance between the nozzle and the obstacle increases, the blower power may be increased.

Furthermore, the speed with which the nozzle is moved may be decreased to achieve uniform treatment of the surfaces according to the distance thereof from the nozzle.

Preferably, the blower power is regulated by varying the number of revolutions of one of the impellers thereof.

A possible operation method may foresee the use of a nebulizer 6 generating a constant amount of mist over time.

The blower power is regulated (for example, through the speed of the impeller thereof) to obtain a point-of-impact air or flow speed which is essentially constant regardless of the distance of the obstacles from the nozzle, and which is a predetermined value.

For example, the point-of-impact air speed may be 1 m/s (but this value, as stated earlier, is only an example; in fact, the flow speed at the point of impact with a surface to be sanitized may also differ depending on the amount of liquid nebulized during the period of time by the nebulizer).

The number of blower revolutions required to obtain a certain flow impact speed with a certain distance may be taken from a table established from experimental tests. This table may be essentially represented by a curve correlating the impeller speed with the nozzle distance, at a predetermined constant impact speed.

For example, to obtain the target impact speed of 1 m/s at a distance (measured by the distance detector(s) L1-L4) of 1 m, the impeller may be activated at 1000 rpm. For a distance of 2 metres, in order to obtain the same target speed of 1 m/s, the impeller may be activated at 3000 rpm. To obtain the target impact speed at 5 metres, meanwhile, the impeller speed may be 10,000 rpm and so on.

In essence, the impeller speed necessary to obtain a predetermined flow speed in the impact area (with the latter a certain distance from the nozzle) is verified experimentally, and, by means of an experimental table stored in the control unit, the latter can regulate the impeller speed according to the distance measured by the distance detectors at a given instant in order to obtain the desired flow speed at the obstacle.

To regulate the amount of disinfectant solution dispensed over a unit of surface area of the object (for example a predetermined number of cubic millimetres per square centimetre of the object), since the production of aerosol (or mist) by the nebulizer is fixed (or constant over the period of time), nozzle positioning speed is regulated around one or both controlled axes R, A.

In essence it is possible to keep the nozzle pointed at a zone which is far from the nozzle (and therefore with a larger surface area) for longer than when treating an area near the nozzle (and therefore with a lesser impact surface area).

Therefore, when treating an area which is far from the nozzle (with the distance given by distance detectors L), the impeller speed may be increased and nozzle positioning speed may be decreased along one or both axes R, A. In order to treat an area near the nozzle, the impeller speed may be decreased and the nozzle positioning speed increased at the same time, around one or both axes R, A.

This method of moving the nozzle and regulating the blower power makes it possible to treat areas located at different distances from the nozzle, essentially with the same amount of disinfectant solution.

The operating method described above reduces the possibility of 'staining' the point of impact of the flow of air and disinfectant or sanitizing particles. In fact, with fine regulation of the impeller power (and—as seen above—of the nozzle positioning speed around one or more of the axes thereof) it is possible to make the flow originating from the nozzle only 'rest' on any obstacle encountered (wall or ceiling of the environment), preventing a staining effect caused by the coalescence of the aerosol particles blending upon impact with the surface facing the nozzle.

Moreover, the method of regulating the impeller power according to the distance of an obstacle from the nozzle makes it possible to obtain an 'impression' D (see FIG. 6) which has an essentially constant surface area even though the distance between the nozzle 4 and the obstacle (the perimeter wall 141 and the ceiling 140, in the case of the drawing) changes according to where the nozzle is oriented.

An operating method for the device equipped with an orientable nozzle 4 which delivers an air flow mixed with disinfectant particles, may comprise the following steps:

a. positioning the nozzle vertically and detecting the distance between the nozzle and the ceiling 140 of the environment to be sanitized (as can be seen in FIG. 6, where the nozzle is oriented towards the ceiling, and the height reading is very close to the reading given by the sensor along the pointing line P);

b. positioning the nozzle horizontally (FIG. 7) and rotating the nozzle by 360°, while detecting, at the same time, the maximum distance 146 and the minimum distance 145 between the nozzle and the side walls;

c. calculating the approximate room volume (for example L×S×H) based on the distances (P, 145, and 146) detected in steps a) and b);

d. regulating the duration of a sanitization cycle, based on the computed volume of the environment.

Since the size of the 'impression' of the flow generated by the nozzle is essentially constant even if the distance between the perimeter walls or the ceiling and the nozzle differs, moving the nozzle in order to sanitize the entire surface area of the walls and ceiling is extremely simple.

For example, a sanitization method may include, in succession or not, the following steps:

a. positioning the nozzle vertically and sanitizing the ceiling of the environment by making a spiral movement with the nozzle; once a perimeter of the spiral has reached a side wall, it is possible to:

b. complete the sanitization of the ceiling by orienting the nozzle in the areas not covered by the spiral movement, preferably by making a serpentine movement with the nozzle;

c. sanitize the walls by orienting the jet thereat and making a serpentine movement with the nozzle.

FIGS. 9 and 10 show a different embodiment of the nozzle. In the said figures, the same reference numbers used earlier are used to denote parts that are functionally similar to those already examined and will not, therefore, be described further.

The embodiment in FIG. 9, shows a nozzle 4' which is supported, for the positioning thereof, by a very similar kinematic mechanism to that shown in FIGS. 1-3. Therefore, at least the movements around the aforesaid R and A axes are possible. The nozzle can also move along the R axis, as described above.

As can be immediately understood from the drawings, the mist line 9' (hose), which transports the mist to the nozzle 4', and the hose 50, which connects the nozzle 4' with the blower delivery line, are no longer concentric, but run essentially parallel to the support 32 and to the second 20 and first body 31.

The nozzle has a Y shape and mixes the mist and the air produced by the blower in proximity to the very nozzle 4'.

Note that in FIG. 9, only the rod 34 connecting the first body 30 to the gear motor is visible, while the rod connecting the second body 31 to the support 32 (although present) is not visible.

The invention also relates to a method of sanitizing an environment by means of a device such as the one described above, comprising at least the following steps:

a. positioning the device in a closed environment to be sanitized b. acquiring the device's position, for example, using a geolocation system or by manually entering the position of the device c. automatically sanitizing the environment d. and, at the end of the sanitization, generating a report containing a sanitization result, at least the acquired device position, and the sanitization time and date, and—optionally automatically sending the aforesaid data to an external server.

According to one aspect, during the sanitization, a light on the device is activated to show the 'sanitization in progress' status, and, once sanitization is complete, the light changes colour to show the 'sanitization complete' status, the end of sanitization being—optionally—established based on the reading by the sensor S. The activation of the light or indicator on the device may also occur regardless of the generation of the report described above.

According to another aspect, sanitization is activated through a remote device (smartphone, tablet, etc.) located outside the environment to be sanitized and interfaced with the control unit via the communication interface 400, which may be of a wireless kind (for example, Wi-Fi or Bluetooth).

The invention may also relate to an environmental sanitizing device 1 comprising a frame 2 housing a reservoir 7 of a disinfectant liquid 3 and supporting a nozzle 4, the nozzle 4 being associated with a generation system 5, 6 of an air flow within which a plurality of disinfectant liquid particles are suspended so as to sanitize a closed environment in which the device 1 can be positioned, wherein the nozzle is rotatably supported by the frame around at least one axis R, the nozzle rotation around the axis R being obtained by means of at least one motorized driving system 20, 21 controlled by a control unit 100 so that the nozzle can be automatically oriented in at least one desired direction with respect to the frame 2 during a sanitization step.

Preferably, the nozzle 4 is coupled with a handling system 21, 22 controlled by the control unit 100 for its orientation with respect to at least two axes R, A mutually perpendicular, preferably around a first vertical axis R and a second horizontal axis A.

More preferably, the nozzle 4 is coupled with a translation system along the vertical axis R.

For example, in a device according to one or more of the preceding three paragraphs, the generation system comprises a blower 5 and a nebulizer 6 of said disinfectant liquid taken from the reservoir, a flow 5A of the blower and an output 6A of the nebulizer being in fluid communication with the nozzle 4.

In a device according to the preceding paragraph, the nozzle 4 may have, at least in proximity to its outlet section 4A, an annular channel 8, fed by the outlet 5A of the blower, in which a conduit of fog 9 connected to an outlet 6A of the nebulizer 6 and concentric to the annular channel 8 discharges.

In one embodiment the nozzle is fed by a Y-shaped duct leading into the nozzle 4, and with a branch fed by the outlet 5A of the blower and the other branch fed by the outlet 6A of the nebulizer.

For example, a compressor 60 may be provided with a discharge 60A connected to the nebulizer 6 for its supply.

In a possible embodiment, the compressor 60A discharge 60A is connected to an inlet 7B of the reservoir 7.

The outlet 7A of the reservoir 7 may be fluidly connected to a fluid inlet 6B of the nebulizer 6.

The nozzle 4 may be supported by a plate-shaped element 40 provided with guides 41 coupled to the frame, the plate-shaped element being moved along the first vertical axis R by a first gear motor 44 coupled to an endless screw 45, and/or wherein the nozzle 4 is mounted on a slewing ring with vertical axis R driven by a rotating gear 46 through a belt 49 and/or in which the nozzle 4 is supported by a first 30 and second body 31, the first body 30 being hinged to a support 32, and the second body 31 being hinged to the first body 30, the second body being connected to the support 29 via a first connecting rod 33, the first body being connected by a second connecting rod 34 to a gear motor 35 controlling the nozzle rotation around the horizontal axis A.

An embodiment may disclose an environmental sanitizing device 1 comprising a frame 2 housing a reservoir 7 of a disinfectant liquid 3 and supporting a nozzle 4, the nozzle 4 being associated with a generation system 5, 6 of a flow of air within which a plurality of disinfectant liquid particles are suspended, so as to sanitize a closed environment in which the device 1 can be positioned, wherein the generation system comprises a blower 5 and a nebulizer 6 of said disinfectant liquid taken from the tank, a flow 5A of the blower and an outlet 6A of the nebulizer being in fluid communication with the nozzle 4.

The nozzle 4 may have, at least in proximity to its outlet section 4A, an annular channel 8, fed by the outlet 5A of the blower, in which a conduit of fog 9 connected to an outlet 6A of the nebulizer 6 and concentric to the annular channel 8 discharges.

The nozzle may be fed by a Y-shaped duct leading into the nozzle 4, and with a branch fed by the outlet 5A of the blower and the other branch fed by the outlet 6A of the nebulizer.

In the embodiment described, an air compressor 60 may be provided, the deliver 60A of which is connected to the nebulizer 6 for its compressed air supply, the nebulizer 6 being configured to produce a continuous flow of fog.

For example the compressor 60A discharge 60A is connected to an inlet 7B of the reservoir 7 for pressurizing it.

An outlet 7A of the reservoir 7 may be fluidly connected to a fluid inlet 6B of the nebulizer 6.

For example, between the compressor 6A and the inlet 7B of the reservoir 7 a solenoid valve 80 is placed, the solenoid valve being controlled by a control unit 100 to control the compressed air flow to the reservoir 7, and optionally a flow meter 88.

In the embodiment, the control unit 100 may control controls the solenoid valve 80 so that the fog generated by the nebulizer 6 contains a constant quantity of disinfectant solution in the time unit.

A method is disclosed for sanitizing an environment by means of an air flow within which a plurality of disinfectant liquid particles is suspended, characterized in that the air flow within which a plurality of disinfectant liquid particles is suspended is generated by combining a stream of air coming from a blower and a mist flow coming from a nebulizer.

According to the method, the nebulizer may generate the flow of mist through compressed air.

In another embodiment, the environmental sanitizing device 1 may comprise a frame 2 housing a reservoir 7 of a disinfectant liquid 3 and supporting a nozzle 4, the nozzle 4 being associated with a generation system 5, 6 of a flow of air within which a plurality of disinfectant liquid particles are suspended, so as to sanitize a closed environment in which the device 1 can be positioned, characterized in that the generation system comprises at least one blower 5, and the nozzle 4 comprises, at least in the vicinity of its output section 4A, an annular channel 8 fed by the flow of the blower free of disinfectant solution particles, the annular channel 8 surrounding, at least in the vicinity of a nozzle outlet 4, a mist conduit 9 fed by an air flow mixed with disinfectant particles, so that the air flowing through the annular channel 8 may confine the flow of air mixed to disinfectant particles.

Possibly, the mist conduit 9 is fluidly connected to the outlet 6A of a nebulizer 6 of said disinfectant liquid, the nebulizer 6 creating a flow of mist of disinfectant liquid.

By way of example an air compressor 60 is provided, whose discharge 60A is connected to the nebulizer 6 for its supply.

The compressor 60A discharge 60A may be connected to an inlet 7B of the reservoir 7.

Possibly, an outlet 7A of the reservoir 7 is fluidly connected to a fluid inlet 6B of the nebulizer 6.

For example, a solenoid valve 80 is placed between a compressor 6A and an inlet 7B of the reservoir 7, the valve being controlled by the control unit 100 to regulate the flow of compressed air to the reservoir 7.

For example, the control unit 100 may control the solenoid valve 80 so that the fog generated by the nebulizer 6 contains a constant quantity of disinfectant solution in the time unit.

In a possible embodiment, the nozzle is rotatably supported by the frame around at least one axis R, the nozzle rotation around the axis R being obtained by means of at least one motion system 20, 21 controlled by a control unit 100 so that the nozzle can be automatically directed in at least one desired direction with respect to the frame 2 during a sanitization phase.

For example, the nozzle is coupled with a motion system 21, 22 controlled by the control unit 100 for its orientation with respect to at least two axes R, A mutually perpendicular, preferably around a first vertical axis R and a second horizontal axis A.

A further embodiment disclose an environmental sanitizing device 1 comprising a frame 2 housing a reservoir 7 of a disinfectant liquid 3 and supporting a nozzle 4, the nozzle 4 being associated with a generating system 5, 6 of an air flow within which a plurality of disinfectant liquid particles are suspended, so as to sanitize a closed environment in which the device 1 can be positioned, characterized in that it comprises a control unit 100 associated with an identification system 400, 401 of the position of the device 1, and configured to generate a report of a sanitizing of the environment where the device 1 is positioned.

It may comprise, a GPS detector 401 of the position of the device 1.

The position of the device 1 may be sent by a remote device to a communication interface 400 connected to the control unit.

The control unit may be interfaced with a sensor S suitable for detecting the amount of disinfectant solution particles present in the aspirated air from the device 1 to determine whether a sanitizing process of the environment is completed or not.

For example a signal light 120 is present, the control unit 100 being configured to control the status of the signal light to indicate the state of progress or completion of a sanitizing process, and/or wherein the control unit is configured to control the signal light based on a reading of the sensor S.

Optionally, there is an RFID reader 105 interfaced with the control unit 100 to acquire the data present in an RFID tag 106 associated with the removable reservoir 7.

For example the report may comprise one or more of the following information: device location, location description, date and time of sanitization, result of sanitization, duration of sanitizing, amount of liquid used for Sanitation, production date, batch production and place of production of the liquid for sanitation.

A Method for sanitizing an environment is disclosed by means of a device according to one or more of the preceding claims, comprising at least the steps of:
 a. placing the device in a closed environment to be sanitized
 b. acquiring the position of the device
 c. automatically sanitize the environment
 d. and at the end of the sanitization process, generating a report containing a result of the sanitization, at least the acquired device position, the time and date of sanitization, and optionally automatically send it to an external server.

In a possible variant of the method, during sanitization a light is activated on the device, indicating the current sanitization state, and, once sanitization is completed, the state of the light is changed to indicate that the sanitization process is ended, the ending of sanitization process being optionally set on the basis of the reading of the sensor S.

For example, the sanitizing process is started through a remote device located outside the environment to be sanitized, by the communication interface 400 of the control unit 100.

Various embodiments of the innovation have been disclosed herein, but further embodiments may also be conceived using the same innovative concept.

The invention claimed is:

1. A method of sanitizing an environment by means of an environmental sanitizing device having an automatically orientable nozzle which discharges an air flow within which a plurality of disinfectant particles is suspended, comprising the steps of:
 a. pointing the automatically orientable nozzle in a predetermined direction, and detecting the distance between the automatically orientable nozzle and an obstacle facing the automatically orientable nozzle, wherein rotation positioning speed of the automatically orientable nozzle around controlled axes is adjusted as a function of the distance between the obstacle and the automatically orientable nozzle, and then
 b. adjusting speed of the air flow with plurality of disinfectant particles suspended therein leaving the automatically orientable nozzle as a function of the detected distance to inhibit coalescence of disinfectant particles on the obstacle facing the automatically orientable nozzle, wherein the adjusting the speed of the air flow comprises:

- lowering power of a blower for the air flow as a result of a movement of the automatically orientable nozzle that decreases the distance between the automatically orientable nozzle and the obstacle, and
- increasing power of the blower for the air flow as a result of a movement of the automatically orientable nozzle that increases the distance between the automatically orientable nozzle and the obstacle.

2. The method according to claim 1, wherein prior to a sanitization phase performing steps of:

- a. positioning the automatically orientable nozzle vertically and detect the distance between the automatically orientable nozzle and a ceiling of an environment to be sanitized;
- b. positioning the automatically orientable nozzle horizontally and rotating it by 360°, while detecting the maximum distance and the minimum distance between the automatically orientable nozzle and side walls;
- c. calculating an approximate room volume based on the distances detected in steps a) and b);
- d. adjusting an amount of disinfectant liquid to be delivered during a cycle of sanitization, based on a calculated room volume of the environment.

3. The method according to claim 1, further comprising adjusting an amount of disinfectant liquid delivered during a sanitization cycle by adjusting duration of the sanitization cycle.

4. The method according to claim 1, wherein said lowering and increasing of the power of the blower comprises varying rotational speed of an impeller of the blower.

5. The method according to claim 1, wherein rotation positioning speed of the automatically orientable nozzle around controlled axes is adjusted, as a function of the distance between the obstacle and the automatically orientable nozzle, to increase the rotation positioning speed when the distance decreases and to decrease the rotation positioning speed when the distance increases.

6. The method according to claim 1, wherein the speed of the air flow leaving the automatically orientable nozzle is adjusted by adjusting the power of the blower injecting air into the automatically orientable nozzle.

7. The method according to claim 6, wherein prior to a sanitization phase performing steps of:

- a. positioning the automatically orientable nozzle vertically and detecting the distance between the automatically orientable nozzle and a ceiling of an environment to be sanitized;
- b. positioning the automatically orientable nozzle horizontally and rotating the automatically orientable nozzle by 360°, while detecting the maximum distance and the minimum distance between the automatically orientable nozzle and side walls;
- c. calculating an approximate room volume based on the distances detected in steps a) and b);
- d. adjusting an amount of disinfectant liquid to be delivered during a cycle of sanitization, based on the a calculated room volume of the environment.

8. The method according to claim 6, further comprising adjusting an amount of disinfectant liquid delivered during a sanitization cycle by adjusting duration of the sanitization cycle.

9. The method according to claim 6, wherein rotation positioning speed of the automatically orientable nozzle around controlled axes is adjusted as a function of the distance between the obstacle and the automatically orientable nozzle, to increase the rotation positioning speed of the automatically orientable nozzle when the distance decreases and to decrease the rotation positioning speed of the automatically orientable nozzle when the distance increases.

10. The method according to claim 1, wherein the environmental sanitizing device comprises:

- the automatically orientable nozzle and a frame,
- the frame housing a reservoir of a disinfectant liquid and supporting the automatically orientable nozzle,
- the automatically orientable nozzle associated with the blower being a generation system of an air flow within which a plurality of disinfectant liquid particles are suspended so as to sanitize a closed environment in which the environmental sanitizing device can be positioned,
- wherein the automatically orientable nozzle is movable relative to the frame, and is associated with a positioning system having at least one motor controlled by a control unit for the orientation of the automatically orientable nozzle with respect to at least two mutually perpendicular axes so as to automatically orient the automatically orientable nozzle in a desired direction with respect to the frame during a sanitization step, the automatically orientable nozzle being coupled with at least one distance detector able to determine the distance between the automatically orientable nozzle and an obstacle facing the nozzle.

11. The method according to claim 10, wherein a pointing line of the at least one distance detector is outside the air flow emitted by the automatically orientable nozzle.

12. The method according to claim 10, wherein a first and a second distance detector are positioned at the sides of the automatically orientable nozzle so that the first distance detector is operative when the automatically orientable nozzle rotates towards the first distance detector while the second distance detector is operative when the automatically orientable nozzle rotates in an opposite direction.

13. The method according to claim 10, wherein a third and a fourth distance detector are positioned below and above the automatically orientable nozzle so that the third distance detector is operative when the automatically orientable nozzle rotates towards the third distance detector while the fourth distance detector is operative when the automatically orientable nozzle rotates in an opposite direction.

14. The method according to claim 10, wherein the generation system comprises the blower controlled by the control unit, the control unit being configured to adjust the power of the blower as a function of the distance detected by the at least one distance detector.

15. The method according to claim 10, wherein the at least two mutually perpendicular axes comprise a vertical axis and a second horizontal axis, wherein the automatically orientable nozzle is associated with a first motor of the at least one motor of the positioning system, the first motor being controlled by the control unit for the orientation of the automatically orientable nozzle around the vertical axis, and wherein the automatically orientable nozzle is associated with a second motor of the at least one motor of the positioning system, the second motor being controlled by the control unit for orientation of the automatically orientable nozzle around the second horizontal axis so as to automatically orient the automatically orientable nozzle in the desired direction with respect to the frame during the sanitization step.

16. The method according to claim 10, wherein the automatically orientable nozzle is supported by a plurality of bodies hinged together, the plurality of bodies being coupled to the at least one motor of the positioning system by a plurality of connecting rods that transmit movement to the plurality of bodies for controlling rotation of the automatically orientable nozzle about a horizontal axis of the at least two mutually perpendicular axes.

17. The method according to claim 10, wherein to generate the air flow within which the plurality of disinfectant particles is suspended, the automatically orientable nozzle is in fluid communication with a delivery line on the blower and with a nebulizer for the disinfectant liquid taken from the reservoir, wherein the automatically orientable nozzle has in proximity to an outlet section of the automatically orientable nozzle an annular channel supplied by the delivery line on the blower in which a mist line extends, the mist line connected to an outlet of the nebulizer.

18. The method according to claim 1, further comprising regulating a positioning speed of the automatically orientable nozzle to inhibit coalescence of disinfectant particles upon impact with the obstacle facing the automatically orientable nozzle to thereby prevent staining.

* * * * *